United States Patent [19]

Chen

[11] Patent Number: 4,518,052
[45] Date of Patent: * May 21, 1985

[54] APPARATUS FOR AUTOMATICALLY MEASURING HEIGHT

[76] Inventor: Li-Fu Chen, 4th Fl., No. 17, La. 133, Pao Pyng Rd., Yuan Ho City, Taiwan

[*] Notice: The portion of the term of this patent subsequent to Jun. 29, 1999 has been disclaimed.

[21] Appl. No.: 397,864

[22] Filed: Jul. 13, 1982

[51] Int. Cl.³ .............................................. G01G 19/00
[52] U.S. Cl. ................................ 177/245; 200/85 R; 200/DIG. 2; 250/202
[58] Field of Search ................... 177/245, DIG. 6, 3, 177/177, 250, 241; 200/DIG. 2, 85 R; 250/202, 215, 221, 234, 235; 33/125 A

[56] References Cited

U.S. PATENT DOCUMENTS

| | | |
|---|---|---|
| 3,163,758 | 12/1964 | Treacy . |
| 3,366,944 | 1/1968 | Cochran ............... 200/85 R X |
| 3,593,030 | 7/1971 | Jaskowsky . |
| 3,899,255 | 8/1975 | Meier ...................... 33/125 A |
| 3,968,848 | 7/1976 | Cherney ................ 177/DIG. 6 |
| 4,154,000 | 5/1979 | Kramer . |
| 4,333,044 | 6/1982 | Blitchington . |
| 4,336,855 | 6/1982 | Chen ............................. 177/245 |

FOREIGN PATENT DOCUMENTS

| | | | |
|---|---|---|---|
| 661580 | 5/1938 | Fed. Rep. of Germany ...... 177/245 |
| 521101 | 5/1940 | United Kingdom ............... 177/245 |

Primary Examiner—Harold Broome
Assistant Examiner—M. J. Reinhart
Attorney, Agent, or Firm—Cushman, Darby & Cushman

[57] ABSTRACT

This invention relates to a body height and weight measuring machine, which operates by means of a winding transmission cord means to drive a sliding plate having sensing, measuring, and digital display functions. When the sliding plate moving upwards, the sensing means will receive the refracted infrared rays as a result of a person's height to cause said winding transmission cord means to stop moving; then, a correct height and weight will be displayed thru digital display means. The aforesaid height measurement and its digital display are done by means of a photocell sensing means being coupled to a scale plate that includes a black and transparent strip in alternate arrangement and equal width so as to have said photocell sensing means generating a forward or reverse sequence sensing signal during the sliding plate moving; then, said signals will be shown on a display means driven with driving circuit.

7 Claims, 11 Drawing Figures

APPARATUS FOR AUTOMATICALLY MEASURING HEIGHT

BACKGROUND OF THE INVENTION

This invention aims to improve the original preceding application case in the digit of display position and the sensing method. In the preceding case, the digital display is positioned at a fixed point on the apparatus. If it is too high, a short person has to raise his (or her) head to read the digits displayed; if it is too low, a tall person has to lower his head to read the digits. Further, said motion of raising or lowering one's head is liable to cause some errors in measuring the body height. The best position of said digital display for obtaining accurate height measurement is within the range higher no more than that of the forehead of an average person. The digital display means in the preceding case generates signal by means of the metal contact point being touched with the sliding PCB: the touch between said metal contact point and said PCB has to be accurate and smooth. When assembling them, special care must be taken on their positions without any error; otherwise, bad contact or tear and wear may be resulted to cause the whole expensive machine to become unserviceable.

DESCRIPTION OF PREFERRED EMBODIMENT

Figure 1:
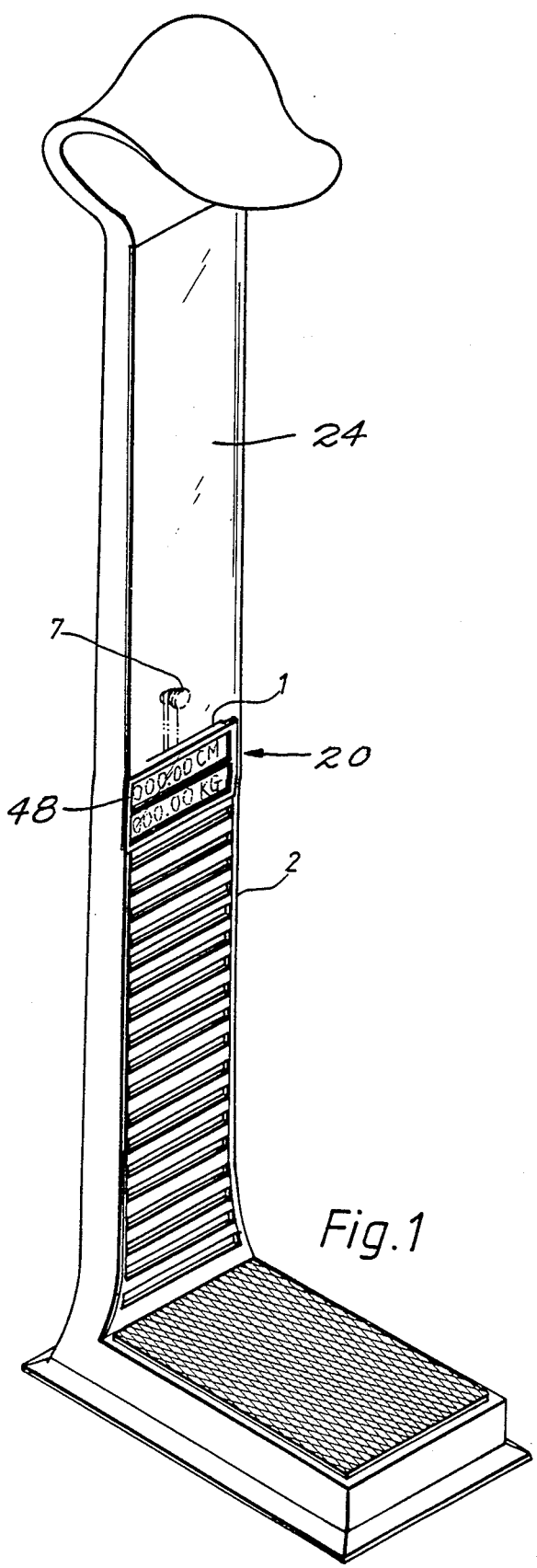
FIG. 1 shows a perspective view of an embodiment in this invention.
Figure 2:
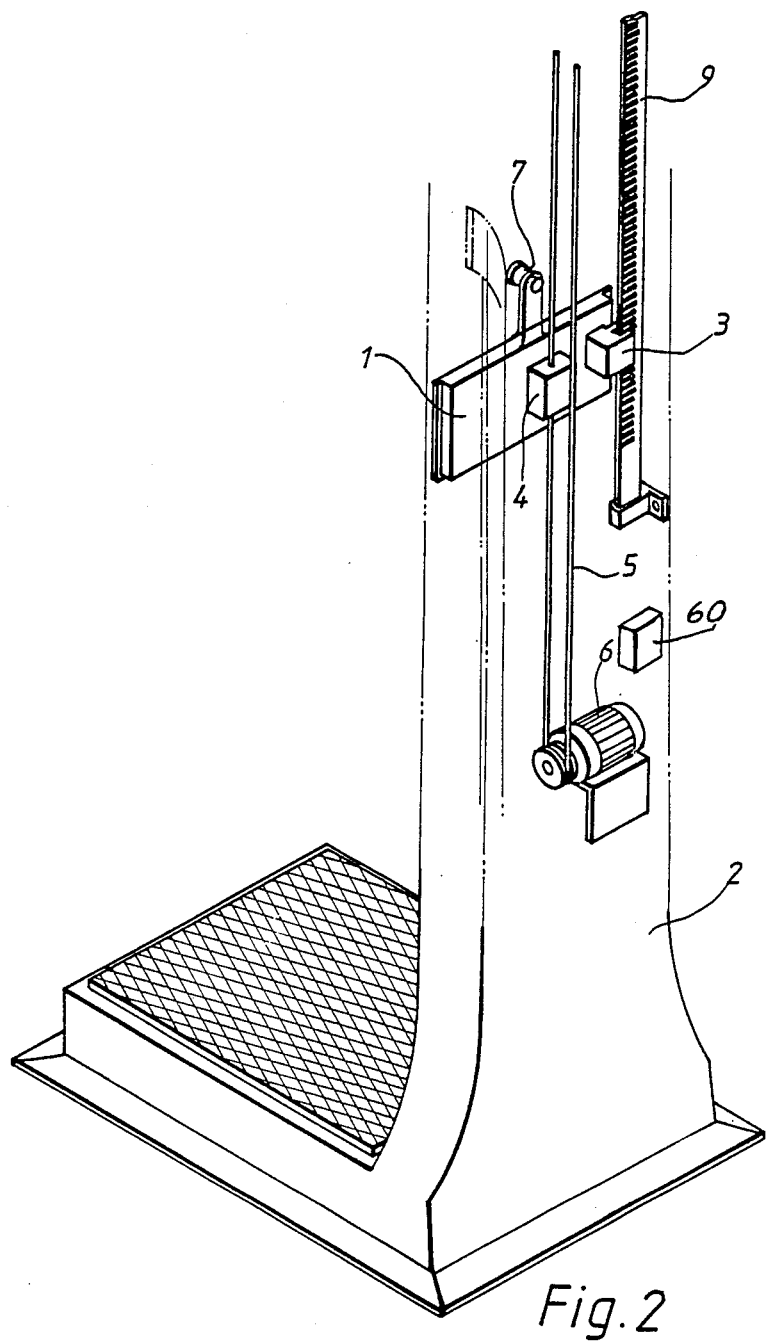
FIG. 2 shows a configuration view among the transmission mechanism, the photocell sensing means, and the scale plate of an embodiment in this invention.
Figure 3:
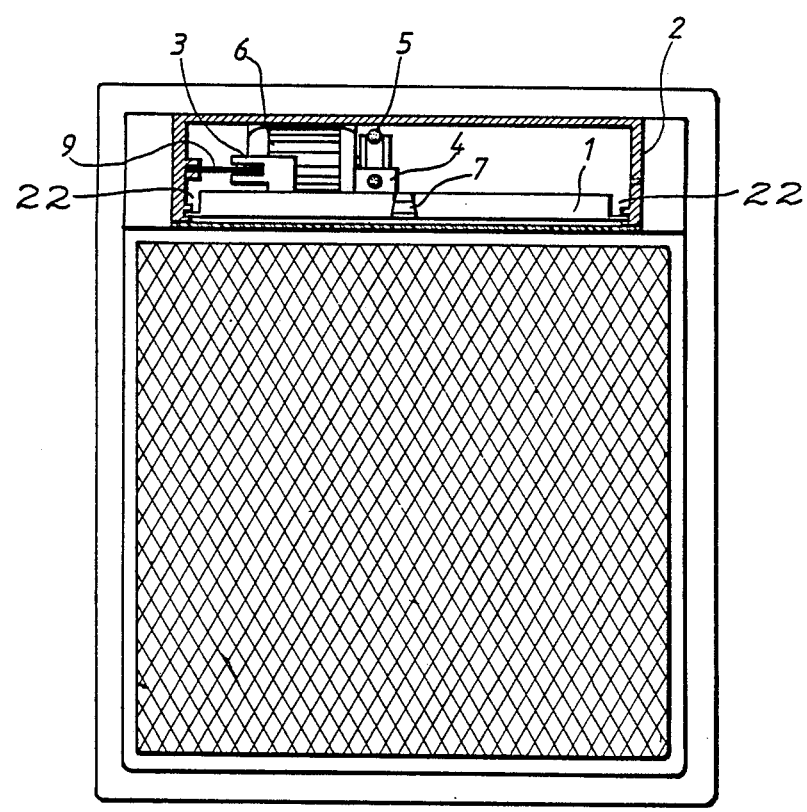
FIG. 3 shows a top and sectional view of this invention.

In this invention, the digital display means is positioned on the sliding plate (1) as shown in FIGS. 1, 2, and 3. The sliding plate (1) may slide up and down along the guide groove at the side of said body (2). At the back of said sliding plate (1), a photocell sensing means (3) and a sliding guide base (4) are mounted; said sliding guide base is fixedly attached to a winding transmission cord (5) so as to have the whole sliding plate (1) being driven with a motor (6) to move up and down along the guide groove at the body (2) side. The starting, stop, reverse rotation and stop controls to the motor (6) are the same as those of the preceding case.

Upon the motor (6) being started, it will rotate forwards to have the sliding plate (1) moving upwards; as soon as the sensor (7) on said sliding plate (1) sense the infrared rays, the motor (6) will stop; at the same time, a time-interval counter will start to count time. Upon the time counting being over, said motor (6) starts to rotate reversely so as to have said sliding plate (1) moving downwards. As soon as said sliding plate (1) reaches the lowest position, the power supply of said motor (6) will be cut off by a micro-switch to stop the driving power. The position of said infrared sensor (7) is determined with the average heights from the level of eyes to the head top of a person, and said sensor is mounted over the sliding plate (1), and will move together with said plate (1) to timely cut off the power supply of said motor (6) and to start a time-interval counter.

Figure 4:
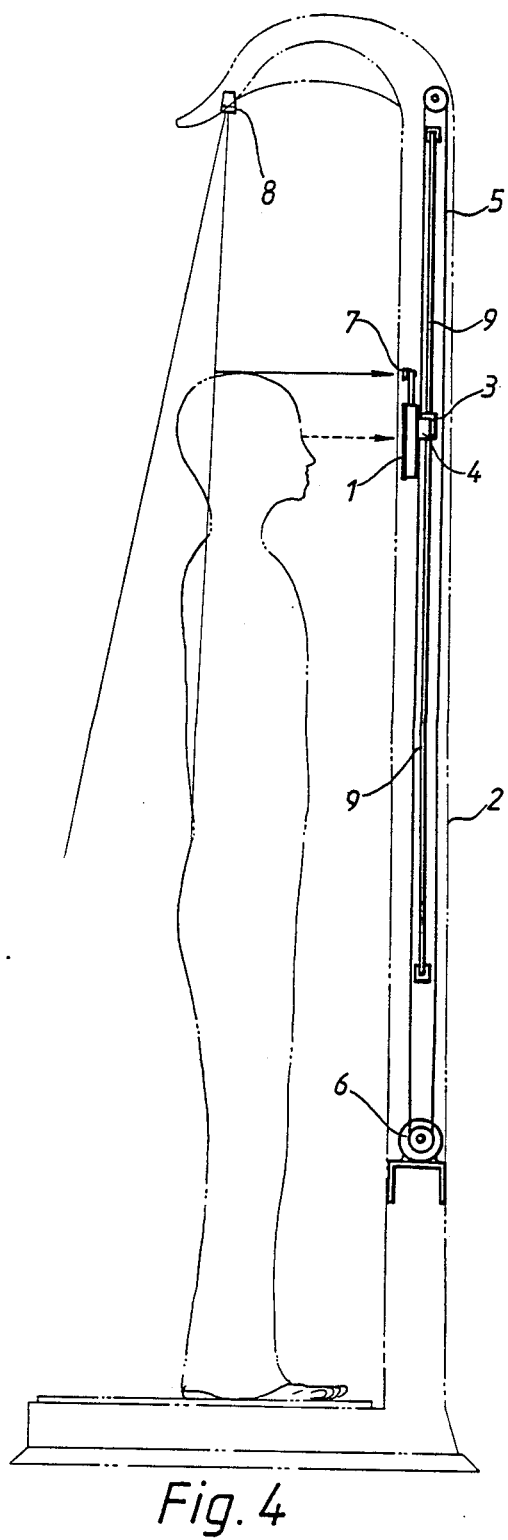
FIG. 4 shows the operation theory by using a special rays and the sensor in an embodiment of this invention.

The theory of sensing the infrared rays is that an infrared emitter (8) being mounted on the top of the body (2) will emit infrared rays at a given downwards slanting angle, as shown in FIG. 4; when said infrared rays throw upon the person's head, said rays will be reflected horizontally to pass thru a transparent glass in the front of said body (2) to have said sensor (7) moving upwards; upon reaching said position and starting to sense the infrared rays, it will trigger a driving function.

Figure 6:
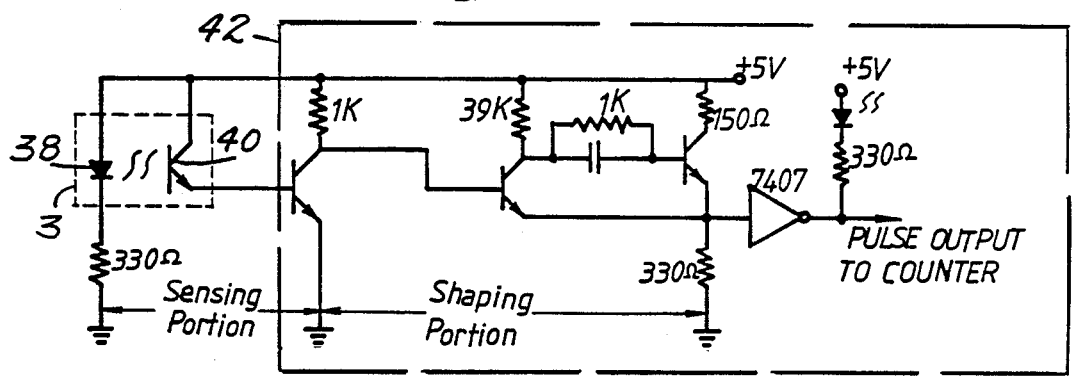
FIG. 6 shows a conventional pulse signal amplification shaping and output circuit used in this invention.
Figure 7:
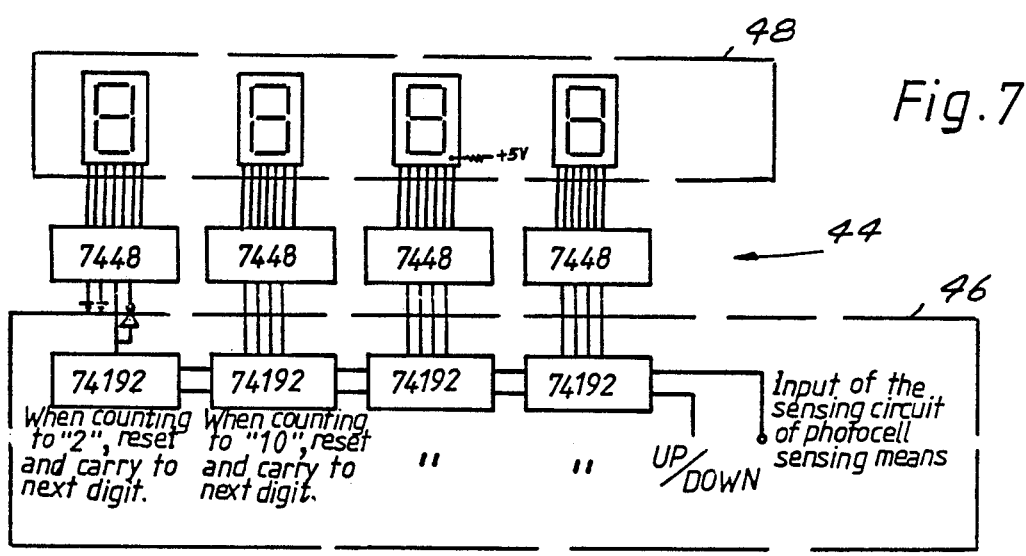
FIG. 7 shows a conventional digital display system used in this invention.

The measuring and digital display means of this invention comprises a photocell sensing means (3) able to slide up and down and a scale plate (9) being furnished with a black and transparent strips in alternate arrangement and equal width and being vertically mounted on said body (2). Said photocell sensing means (3) includes LED and a sensing element, which are correspondingly sliding along the both sides of said scale plate (9) respectively. By means of an intermittent light-throwing method, a digital display circuit in said sliding plate (1) is driven to display a number of digits on a quantitative increasing manner, or on a quantitative decreasing manner as shown in FIG. 6. Upon the aforesaid LED and sensing element being coupled and sliding over said scale plate (1), said sensing element will detect the light on an intermittent manner because of on/off light passing nature of said scale plate (1); as a result, an intermittent output voltage will be generated to pass thru a shaping circuit, and then a pulse is delivered into a counter as shown in FIG. 7. Said counter is installed inside the sliding plate (1), and its digital display is at the front panel of said sliding plate (1).

The aforesaid digital display means may, if necessary, be set with a lowest point to start digit display and a highest point to start the digit display in accordance with the length of said scale plate (9). In accordance with the using occasion and precision requirement, said scale plate (9) may be provided with further fine scales; simultaneously, the digit carrying system in the display means should also be modified to adapt to said fine scale plate so as to be able to indicate further precision height measuring function.

Figure 5:
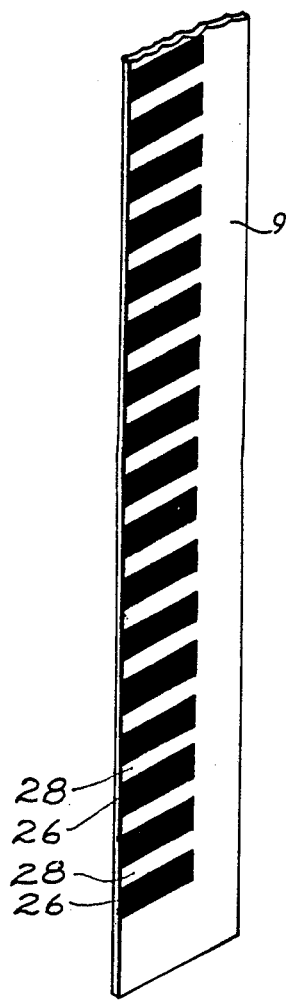
FIG. 5 shows a perspective view of the scale plate in an embodiment of this invention.
Figure 8:
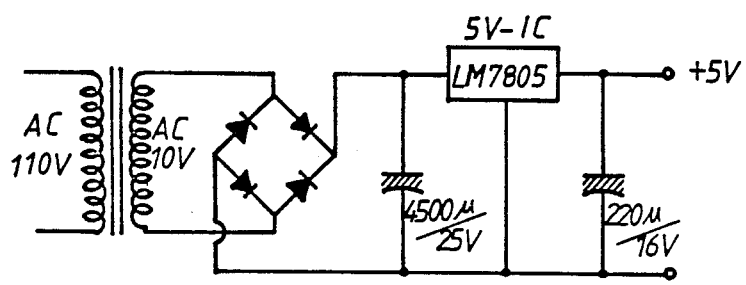
FIG. 8 shows a conventional power supply circuit used for UP/DOWN driving function in this invention.

Upon said time-interval counter being stopped, and the motor (6) rotating reversely to drive said photocell sensing means (3) moving downwards, the digital display circuit in this invention may instruct the UP/DOWN control circuit (shown in FIG. 8) of the power supply to generate a voltage output in a manner of intermittent "LOW—HIGH—LOW—HIGH" so as to have said counter making reverse counting; in other words, when the photocell sensing means (3) moving downwards and coupling to said scale plate (9), said digital display circuit may be driven to perform a quantitative decreasing digital display, or another set of LED and sensing element may be furnished in said photocell sensing means (3) to adapt to the scale plate (9) (shown in FIG. 5) at the corresponding position for driving said digital display circuit to perform quantitative decreasing digital display.

Briefly, as soon as the motor is started to rotate, the light emitter (8) on the machine top, and the digital display circuit and the photocell sensing means (3) in said sliding plate (1) will be driven simultaneously; now, the digits of body height displayed in the front of said sliding plate (1) will be increased quantitatively because of the photocell sensing means (3) driving the digital display circuit. Upon said sensor (7) receiving the infrared rays refracted from the person's head top under measuring, the power supply of motor (6) will be cut off immediately, and simultaneously a time-interval counter will also be actuated. Now, the digits displayed in the front face of said sliding plate (1) will be the height and the weight of the person under measuring.

Upon the time counting being over, the motor (6) will rotate reversely to drive the sliding plate (1) downwards; simultaneously, said photocell sensing means (3) will also drive the digital display circuit to make quantitative a decreasing digital display.

Figure 9:
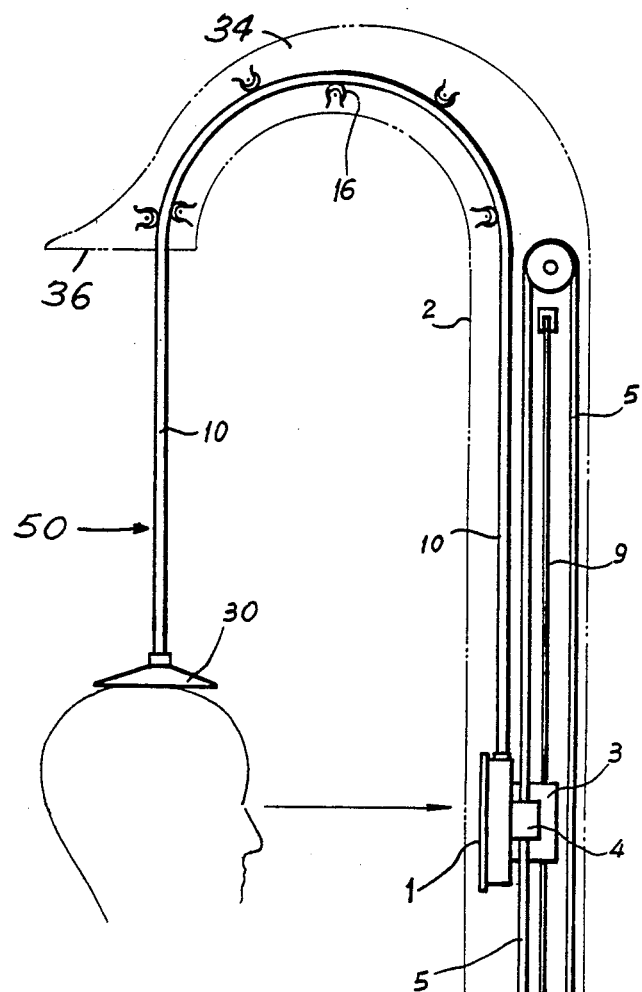
FIG. 9 shows the structure of an embodiment of the touch means to stop said sliding plate.
Figure 10:
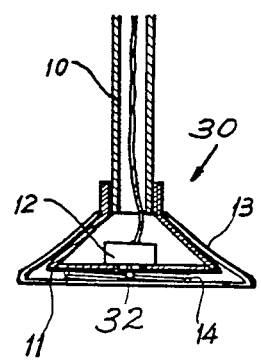
FIG. 10 shows the micro switch assembly at the end of the hose in this invention.

The stop control of said sliding plate (1) during sliding may also be done by using a touch means to cut off the power of said motor (6) as shown in FIG. 9, of which the structure comprises a flexible hose (10) extended out with a suitable length from said sliding plate (1) to the top of the machine body (2) at an angle of 180°, and hanging over the head of a person to be measured. At the end of said hose, there is a cup lid assembly as shown in FIG. 10, which includes a conic base (11), a micro-switch (12), a soft lid (13) and a spring (14). The touch piece of said micro-switch (12) is hung out downwards to have a suitable space to the soft lid (13) with a spring (14) between them.

Figure 11:
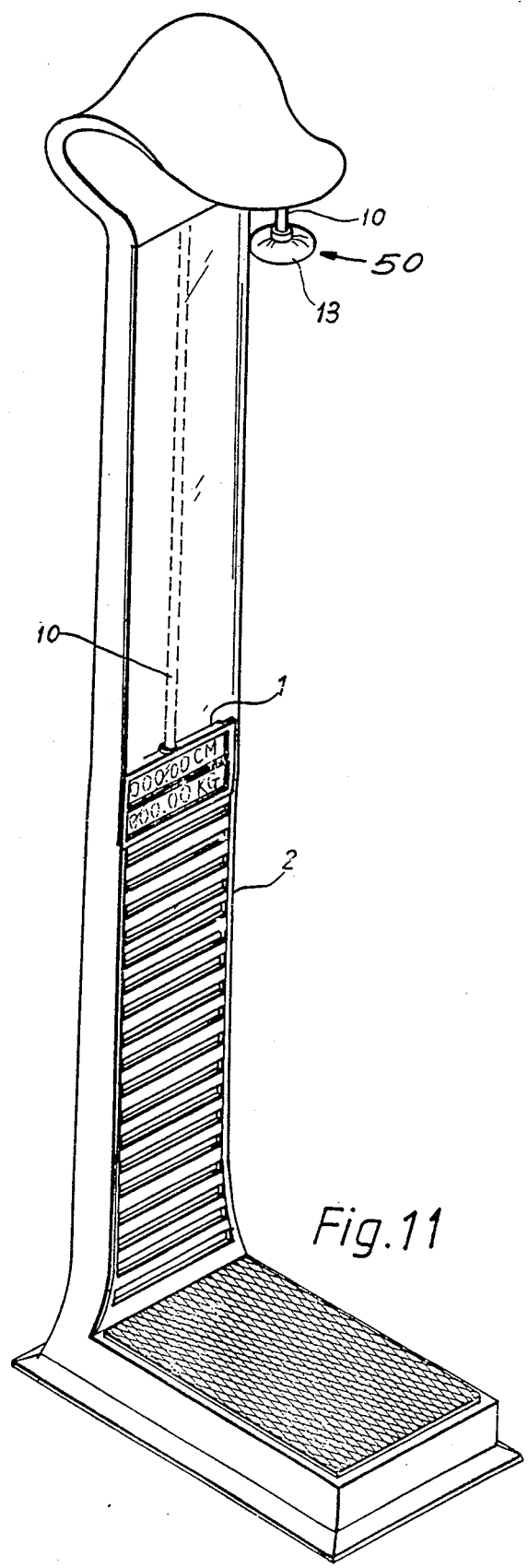
FIG. 11 shows the outer view of an embodiment of the whole touch-control type of said automatic digital display machine for measuring height weight in this invention.

The operation of said touch control is that, when the cup lid assembly sliding downwards as shown in FIG. 11, the person's head will touch said soft lid (13) and said micro-switch (12) to cut off the power supply of said motor (6). The hose (10) in the aforesaid means is used for replacing the sensor (7), and for saving the emitter (8). Along the passage of said hose (10), a suitable number of rollers (16) are installed to guide said hose for smoothly sliding back and forth. During not performing measurement, said cup lid assembly is tucked under the top cover of this machine body (2), while the sliding plate (1) is at its lowest position. Upon a person standing at the measuring position and turning on the power supply of said motor (6), said sliding palte (1) will be pulled upwards, while said up lid assembly moves downwards. In the control circuit of said means, its output voltage sequence is reversely different from the aforesaid method of using light emitter (8) and sensor (7), i.e., when the photocell sensing means (3) on said sliding plate (1) sliding upwards along said scale plate (9) having black-and-transparent strips in alternate arrangement and equal width, said control circuit will generate an "LOW—HIGH—LOW—HIGH" output voltage to cause the counter in said sliding plate (1) to show a quantitative decreasing digital display.

Further, upon said soft lid (13) of the cup lid assembly touching the head top of a person under measuring, said spring 8149 will be retracted because of the softness of said soft lid (13) to reduce the space between the bottom of said conic base (11) and the soft lid (13), and to trigger said micro-switch (12) to cut off the power supply of the motor (6) and simultaneously to actuate the time-interval counter. At that time, the digits indicated in the front of the sliding plate (1) are the height and weight of the person under measuring. As soon as the time counting is completed, and the digital display is discontinued, and the head of person under measuring is disengaging with said cup lid assembly, said spring (14) will release said micro-switch to turn on the power supply of said motor (6). Upon said starting to rotate reversely, said cup lid assembly and the sliding plate (1) will be returned to their original positions.

The advantages and features of the present invention are as follows:

(1) The digital display screen is installed on the sliding plate (1), and the distance between said sensor (7) and said digital display screen is similar to that from the eye level to the head top; thus, the figures of body height to be seen by the person under measuring are much accurate.

(2) Since the sensing means in this invention is a photocell sensing means (3), being slid along the both sides of said scale plate (9), its precision requirement is rather low; therefore, the simple winding transmission cord means will satisfy the requirement.

(3) The sliding movement between the photocell sensing means (3) and said scale plate (9) is a non-contact type; therefore, it has a low precision requirement, and has no wear and tear problem as well as assembling problem.

(4) During measuring, digits displayed are in a quantitative increasing manner, while the slide plate (1) slides backwards, the digits displayed are in a quantitative decreasing manner.

(5) In the touch means to stop the sliding plate and to display digit, the strength of said spring (14) is constant; the micro-switch (12) would not be triggered until the head of person actually touching; in other words, the person's hair cannot affect the accuracy of the measurement because of it having insufficient force to push the bottom of the cup lid assembly to trigger said micro-switch (12).

I claim:

1. An apparatus for automatically measuring and displaying the height of the top of the head of a human being above a surface, comprising:

a generally vertical frame a first extremity of which is fixed to said surface;

first radiation source means, fixed to a second extremity of said frame, for directing radiation toward the top of the head of a human being standing on the surface;

sliding assembly means, slidably disposed on said vertical frame, for sliding rectilinearly along said vertical frame between said first and second extremities, said sliding assembly means including:

first radiation detecting means for detecting radiation reflected toward the frame by the top of the head of the human being; and display means for displaying indicia of the height of the human being;

drive means, responsive to said detected radiation, for sliding said sliding assembly means along said frame toward said second extremity and for stopping said sliding assembly means at a first position, said first position being determined in response to said detected radiation; and position determining means for determining the position of said sliding assembly means along said frame and for converting said determined position into said indicia of height to be displayed by said display means.

2. An apparatus as in claim 1 wherein said position determining means comprises:
a linear strip fixed to said frame, said strip including means defining encoded indicia of position; and
position indicia sensing means, fixed to said sliding assembly means, for sensing said encoded indicia of position.

3. An apparatus as in claim 2 wherein:
said position encoded indicia defining means optically encodes said indicia; and
said position indicia sensing means includes:
second radiation source means, disposed on a first side of said strip, for transmitting radiation through said strip; and
second radiation detecting means, disposed on a second side of said strip and optically coupled through said strip to said second radiation source means, for detecting the effect of said optical encoding on the radiation transmitted through the strip.

4. An apparatus as in claim 3 wherein:
said optical encoding of said strip includes a pattern of alternating opaque and transparent portions; and
said position sensing means further includes counting means, coupled to said second radiation detecting means, for counting the detected changes caused by said pattern in the radiation transmitted through said strip as said sliding assembly means slides along said frame, the count of said counting means proportional to said indicia of height.

5. An apparatus as in claim 4 wherein said display means continuously displays said count of said counting means.

6. An apparatus as in claim 5 wherein said drive means further includes:
timing means for timing a predetermined interval of time beginning when said sliding assembly means is stopped; and drive means, responsive to said timing means, for sliding said sliding assembly means toward said first extremity after said predetermined interval has elapsed.

7. An apparatus as in claim 1 wherein said displayed indicia of said display means includes a digital display indicator fixed to said sliding assembly means at a position such that the indicator is at approximately the level of the eyes of the human being when said sliding assembly means stops at said first position.

* * * * *